United States Patent [19]  [11] 4,387,718
Bilitz et al.  [45] Jun. 14, 1983

[54] CONTROL COVER FOR NERVE STIMULATOR

[75] Inventors: Mark R. Bilitz, Minneapolis; Dale A. Dickson, Fridley, both of Minn.

[73] Assignee: Medtronic, Inc., Minneapolis, Minn.

[21] Appl. No.: 259,100

[22] Filed: Apr. 30, 1981

[51] Int. Cl.³ .............................................. A61N 1/00
[52] U.S. Cl. ............................................... 128/419 R
[58] Field of Search .................... 128/403, 419 P, 421, 128/783, 790, 800, 801; 200/42 R, 327, 334, 333; 220/346; 340/365 E, 365 R, 365 VL

[56] References Cited

U.S. PATENT DOCUMENTS 4,005,460 1/1977 Mizukawa ........................... 354/202
4,219,267 8/1980 Suzuki et al. ....................... 354/289

Primary Examiner—Kyle L. Howell
Assistant Examiner—Max F. Hindenburg
Attorney, Agent, or Firm—Merchant, Gould, Smith, Edell, Welter & Schmidt

[57] ABSTRACT

A control cover for a nerve stimulator is moveable between a protective position in which access to the stimulator controls is blocked to prevent accidental alteration of the settings thereof, except for emergency OFF button which remains accessible at all times and a use position in which the controls are accessible for intentional changing of control settings. The disclosed embodiment has a sliding panel which covers a set of keyboard switches. Apertures are provided in the cover and, in one position of the sliding cover, are aligned with the switches to permit access thereto. In the protective position of the cover, the apertures in the cover are moved out of alignment with the switches, preventing access thereto. The OFF switch and its corresponding aperture in the cover are larger than the other switches, so that it remains accessible in both positions of the cover.

10 Claims, 4 Drawing Figures

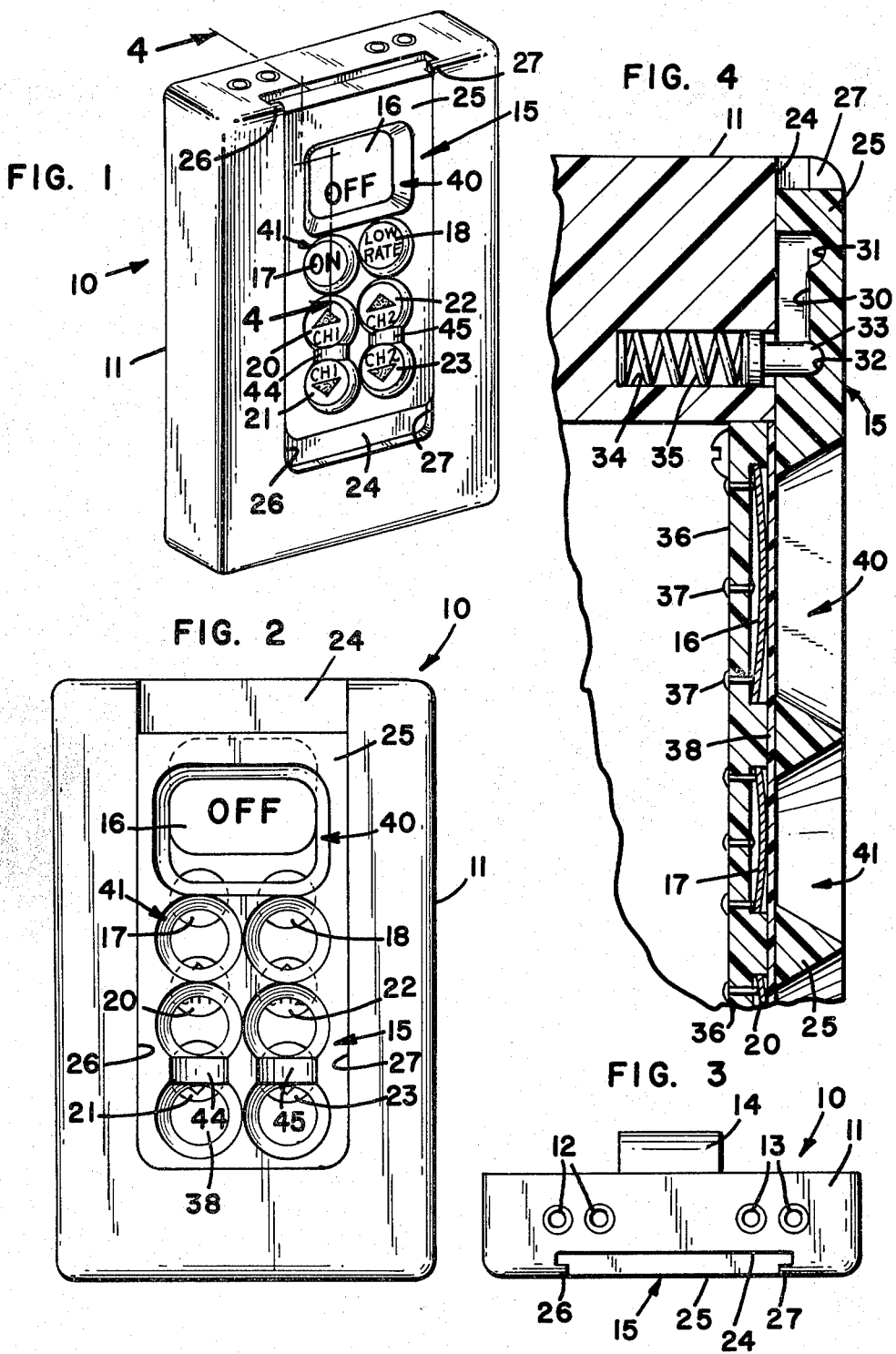

CONTROL COVER FOR NERVE STIMULATOR

FIELD OF THE INVENTION

The invention pertains to the field of nerve stimulators, also referred to as tissue stimulators, used in the field of medicine for the treatment of pain. In particular, the invention pertains to a control cover for the controls of the nerve stimulator, for preventing inadvertent changing of the control settings.

BACKGROUND OF THE PRIOR ART

Nerve stimulators, also referred to as tissue stimulators, have gained wide acceptance in the field of medicine for the treatment of chronic, intractable pain. Nerve stimulators include electrical circuits for generating electrical pulses, and leads and electrodes which convey electrical pulses to the affected part of the body. In the case of non-implantable nerve stimulators, the pulse generating circuitry is usually contained in a box or package adapted to be worn or carried by the patient. Electrical leads connect from the pulse generator to electrodes which are in contact with the body. In the case of transcutaneous nerve stimulators, the electrodes have a significant surface area in contact with the skin, and are held in place by adhesives, etc., over the affected areas. In other cases the leads are introduced through the skin to an implanted electrode, for example along the spinal cord. The electrical impulses produced are applied by the electrodes and produce the desired result of lessening the perceived pain. Controls are usually provided on the pulse generator to control the amplitude of the output pulses, and possibly other parameters to enable the patient to adjust the device for best results. In general, nerve stimulators have achieved wide-spread acceptance because of their ability to deal with pain without the use of drugs and possible harmful side effects.

One problem existing in the use of prior art nerve stimulators is the possibility of inadvertent changing of the pulse generator controls, for example by bumping them. With the pulse generator box clipped on the belt, it is possible to inadvertently brush the controls with the arm, or by bumping into another object, to inadvertently change the control setting, whether potentiometer knobs, push buttons on a key board, etc. This could have the unpleasant effect of suddenly increasing the amplitude of stimulation which could, under some circumstances, be painful to the patient. It is also possible that the settings could be reduced resulting in inadequate blocking or masking of the pain.

SUMMARY OF THE INVENTION

This problem in the prior art is solved by the present invention by providing a protective cover which blocks most of the controls against inadvertent alteration or actuation, while providing at all times access to an OFF switch and providing convenient access to the remaining controls when it is necessary to alter the settings.

These and other advantages are provided in the present invention through the use of a moveable cover.

BRIEF DESCRIPTION OF THE DRAWINGS

In the drawing, FIG. 1 is a view in perspective of a nerve stimulator incorporating the protective cover of the present invention;

FIG. 2 is a plan view of the stimulator of FIG. 1, with the cover moved to the protective position;

FIG. 3 is an end view of the stimulator of FIG. 1, and,

FIG. 4 is an enlarged sectional view taken generally line 4—4 of FIG. 1.

DETAILED DESCRIPTION OF THE PREFERRED EMBODIMENT

In FIG. 1, reference 10 generally designates a nerve stimulator pulse generator. Stimulator 10 consists of a generally rectangular housing or box 11 made of any convenient material, for example plastic. The batteries, electronic control circuitry and electronic pulse output circuitry are all contained within housing 11, and can take any form as is generally known. For example, the control circuitry can take the form of that disclosed in co-pending patent application Ser. No. 258,918 entitled "Keyboard-Controlled Microprocessor-Based Nerve Stimulator" by Dennis Hepp and John Badzinski. A pair of connectors 12 is provided for connection to the leads to the stimulation electrode (not shown). As the device shown in FIG. 1 is a two channel device, a second pair of connectors 13 are provided for the output to the other channel, for connection to the electrode leads for that channel. A belt clip 14 (FIG. 3) can be provided if desired for attachment of the nerve stimulator to the patient's belt or waistband.

The front panel of stimulator 10 has a recess 24 in which the control keyboard 15 is located. The recess in turn is filled and the keyboard partially covered by sliding keyboard cover 25. The keyboard in the embodiment shown includes an OFF or STOP switch 16, an ON switch 17, a LOW RATE switch 18, switches 20 and 21 for increasing and decreasing, respectively, the channel one output, and switches 22 and 23 for increasing and decreasing, respectively, the channel two output. The housing includes flange portions 26 and 27 (FIG. 3) along the edges of the recess area. Cover 25 consists of a panel member having a thickness comparable to the depth of the recess and has cutaway portions along its edges to meet with them and fit around and under flange portions 26 and 27. The flange portions thus serve to prevent cover 25 from coming off of the stimulator. Cover 25 is somewhat shorter than recess 24, and some movement in a direction longitudinally of the cover is permitted. In FIG. 1, cover 25 is moved upward to expose the control switches, and in FIG. 2 cover 25 has been slid downward to block most of the control switches.

As seen in FIG. 4, cover 25 has a slot 30 formed on its underside. Slot 30 extends a distance longitudinally of the cover, and has deepened end portions 31 and 32. A detent member 33 is positioned within a well or bore 34 is housing 11, and its rounded end fits within slot 30. A spring 35 urges the detent 33 towards the cover. The ends of the slot prevent movement of cover 25 off the stimulator, and the deepened end portions of the slot help hold the cover in either of the two end positions.

Also seen in FIG. 4 are portions of switches 16 and 17. In the embodiment shown, these switches consist of snap-action discs trapped within a circuit board 36 and cooperating with a plurality of terminals 37 to make a circuit when depressed. A Mylar film 38 is sandwiched in and contains the printed indicia for the switch functions. Alternatively, a membrane-type switch or any other type of switch can be used rather than the disc type switch, as the exact type of switch is immaterial.

Cover 25 includes a plurality of apertures, one for each switch function. In FIG. 4, apertures 40 and 41, for the OFF switch and ON switch, respectively, are shown. These apertures pass through cover 25 to expose the underlying switch. The walls of the apertures are angled for convenience, although this in not necessary. Also, portion 44 of the cover between the apertures for switches 20-21, and also the portion 45 of the cover between switches 22-23 are rounded out slightly for convenience of the user in moving his finger rapidly from the increase switch to the decrease switch.

When the cover is in the position shown in FIG. 1, access is provided to all switch functions. This enables the user to depress the desired switch, for example channel one increase, decrease, low rate, etc., as desired to adjust operating conditions to optimum effectiveness. After the adjustments are made, sliding cover 25 is moved downward to the position shown in FIG. 2. In that position, the portion of the cover between adjacent apertures obscures of blocks direct access to the switches, except for OFF switch 16. In the position shown in FIG. 2, it is not possible to inadvertently bump the switches, either with the arm or by bumping into another object, so as to unintentionally alter the settings. The OFF switch is of greater size, in a direction longitudinally of the travel of the cover, so that it is not completely blocked by movement of the cover. Therefore, the OFF or STOP switch remains accessible to serve as a "panic switch" in case it is necessary for the patient to turn the unit off quickly. The size of the apertures, the spacing of the switches, and the thickness of the cover of course are adjusted to provide the required degree of accessiblity to switches in the use position and the required blocking of the switches in the protective position of the cover. The length of slot 30 corresponds to half the spacing between adjacent switches so that the remaining switches are blocked as indicated in FIG. 2. The use of the detent and the deepened end portions of slot 30 helps hold the sliding cover in the protective position. Also, the fact that the protective cover is basically flush with the stimulator housing, and has no protrusions, also serves to help hold it in place against the possibility of accidental movement thereof.

The objective of maintaining accessibility to the OFF switch while the other controls are blocked could also be achieved by placing the OFF switch separately from the cover so it is not covered thereby. However, placing the OFF switch under the cover and providing a larger aperture in the cover therefor as shown in the accompanying drawings does have the advantage of providing a location for the OFF switch which can be rapidly accessed by touch without having to look at the unit. In a situation in which is was desired to turn the unit off quickly, the fingers can be moved across the unit until the large aperture is found. Because the other controls remain blocked, there is no danger of inadvertently altering their setting or increasing the output while reaching for the OFF switch.

While the presently preferred embodiment of the invention has been described herein in terms of a sliding cover protecting push button switches on a keyboard, it will be understood that the invention is equally applicable to other configurations also. For example, other types of switches such as rotary, toggle, slide, etc. as well as other types of controls such as potentiometer control knobs, etc. can be protected by the present invention, as can alternate means for moveably securing the cover to the housing. Of course the recess on the stimulator housing might have to be deeper to accommodate the greater thickness of such other types of controls, and the size and spacing of the apertures in the protective cover would be similarly adjusted to accomodate the particular type of controls.

It will be seen from the foregoing description and drawing that we have provided a protective cover for the controls on a nerve stimulator that prevents inadvertent alteration of the control settings which could have unpleasant effects for the user of the device. Neither the control settings nor the protective cover are easily moved or changed by inadvertent brushing or bumping of the nerve stimulator housing by clothing, other objects or other parts of the body. However, the cover may be easily opened by a deliberate movement thereof to provide easy access to alter control settings. An emergency OFF or STOP button for stopping operation of the nerve stimulator remains easily accessible at all times.

What is claimed is:

1. A tissue stimulator, comprising:
   a housing adapted to be worn or carried by a user of the stimulator;
   circuit means contained within said housing for producing output stimulating pulses;
   user operated controls mounted to said housing and electrically connected to said circuit means for controlling the operating thereof; and
   a control cover having apertures through which said controls may be accessed, and means for moveably connecting said cover to said housing with said apertures aligned with the positions of said controls when the control cover is in one position to permit access to the controls, and with the apertures out of alignment with the controls when the control cover is in a second position so that the cover blocks access thereto.

2. A stimulator according to claim 1 wherein said user operated controls include an OFF switch mounted to the housing for access by the user regardless of the position of the cover.

3. A stimulator according to claim 2 wherein said cover extends generally over the OFF switch and has an aperture aligned therewith, and wherein the OFF switch remains accessible to the user regardless of which of said positions the cover is in.

4. A stimulator, comprising:
   a housing having a control panel area and adapted to be worn or carried by a user of the stimulator;
   circuit means within the housing for generating output stimulation pulses for connection to electrodes for application to the body of the user;
   a plurality of user operable controls mounted on said control panel area and electrically connected to said circuit means for controlling the operation thereof; and
   a control cover and means slideably mounting it on the housing generally over said control panel area for movement between first and second positions, said control cover having a plurality of apertures positioned for alignment with said plurality of user operated controls when the cover is in one of said positions to permit access to said controls and for misalignment with said controls when the cover is moved to the other position to block access to said controls.

5. A stimulator according to claim 4, wherein said plurality of user operated controls comprise keyboard switches and wherein said switches include an OFF switch having a larger depressable area than the other of said switches, and wherein said cover has an aperture generally over said OFF switch which is large enough so that the OFF switch remains accessible in any position of said cover.

6. A stimulator according to claim 4, wherein the cover is mounted on the housing generally flush with the surrounding portions of said housing to minimize the possibility of accidental movement of the cover.

7. A stimulator according to claim 4 further including detent means providing engagement between the housing and the cover to releasably hold the cover in the position blocking access to said controls.

8. A stimulator according to claim 4 wherein said cover mounting means comprises flange portions along opposite sides of the housing adjacent said control panel area and mating grooves on said cover to hold the cover on the housing while permitting sliding motion thereof.

9. A stimulator according to claim 8 further including detent means connected to limit sliding movement of the cover between said two positions.

10. A stimulator according to claim 4 wherein the amount of movement of said cover between the first and second positions is approximately half the distance between adjacent ones of said user operated controls, in a direction parallel to the movement of the cover.

* * * * *